United States Patent [19]
Slowiaczek et al.

[11] Patent Number: 5,763,194
[45] Date of Patent: Jun. 9, 1998

[54] CELL SEPARATION DEVICE

[75] Inventors: Peter R. Slowiaczek, Hurstville; Robert E. Nordon, Kensington; Klaus Schindhelm, Cherrybrook; Bruce Milthorpe, Roseville, all of Australia

[73] Assignee: Unisearch Limited, New South Wales, Australia

[21] Appl. No.: 637,673

[22] PCT Filed: Oct. 31, 1994

[86] PCT No.: PCT/AU94/00671

§ 371 Date: Jun. 26, 1996

§ 102(e) Date: Jun. 26, 1996

[87] PCT Pub. No.: WO95/11960

PCT Pub. Date: May 4, 1995

[30] Foreign Application Priority Data

Oct. 29, 1993 [AU] Australia ............................. PM2118
Apr. 29, 1994 [AU] Australia ............................. PM5359

[51] Int. Cl.$^6$ .............................. G01N 33/53; C12Q 1/24
[52] U.S. Cl. .................. 435/7.2; 435/30; 435/287.2; 435/287.3; 435/297.4; 435/308.1
[58] Field of Search ...................... 435/7.2, 30, 287.2, 435/287.3, 297.4, 208.1, 325

[56] References Cited

U.S. PATENT DOCUMENTS 4,828,563  5/1989  Müller-Lierheim ................ 623/16
5,081,030  1/1992  Civin .................................. 435/380
5,474,902  12/1995  Uylen et al. ........................ 435/7.9

FOREIGN PATENT DOCUMENTS

WO 92/18643  10/1992  WIPO.

OTHER PUBLICATIONS

S.B. Kessler. "Adsorptive plasma treatment: optimization . . . " Blood Purification, vol. 11, 1993, pp. 150–157.
Steneker et al. "Electromicroscopic examination . . . " Transfusion, vol. 32 (5), 1992, pp. 450–457.
D. Merlet et al. "Isolement de cellules . . . " C.R. Acad. Sci. Paris, Serie (III)(1990), pp. 565–570.
S. Miltenyi et al. "High gradient magnetic cell . . . " Cytometry, vol. 11, 1990, pp. 231–238.
J. Jackson et al. "Binding of human endothelium . . . " J. Cell Science, vol. 96(2), 1990, pp. 257–262.
R. Alan Hardwick et al. "A large–scale magnetic separator . . . " Artificial Organ, vol. 14(5), 1990, pp. 342–347.

*Primary Examiner*—James Ketter
*Attorney, Agent, or Firm*—Nixon & Vanderhye

[57] ABSTRACT

A method and apparatus for separation of cells including a semi-permeable substrate to which a ligand is attached to its surface which is adapted to bind a desired cell type. The apparatus comprising a semi-permeable substrate in the form of an array of hollow fibres is provided internally with a ligand reactive to the desired cell type.

26 Claims, 10 Drawing Sheets

CELL SEPARATION DEVICE

TECHNICAL FIELD

The present invention relates to a method and apparatus for separation of cells. The apparatus includes a semi-permeable substrate to which a ligand is attached to its surface which is adapted to bind a desired cell type. The invention also relates to cells that are separated by the method or apparatus of the invention.

BACKGROUND ART

Separation of specific cells from a mixed cell population is important for cell biological and immunological studies and for use in medical cell therapy. Small-scale ligand based separation techniques (less than $10^9$ cells) which include fluorescent activated cell droplet sorting and cell panning are unsuitable for medical therapies. Non-ligand based separation techniques such as synthetic fibre leucocyte filters and counter-flow elutriation are not selective or adaptive for separation of specific cell subtypes. Current large-scale ligand based separation techniques such as column chromatography, magnetic bead or microsphere adsorption cannot separate easily and quickly purified cell subtypes for clinical therapies.

Cell depletion techniques for clinical applications have been adequate for large-scale removal of pathogenic cell sub-types, while cell enrichment and expansion culture technologies still require further development. Cell affinity separations are based on the selective absorption of cell phenotype using antibody, lectins, or other moieties specific for cell surface markers. Affinity techniques include plate panning, column chromatography, and magnetic bead or micro-particle absorption. Depletion of cell subsets (>1,000-fold) is possible using magnetic beads. Recovery of adherence cells involves the use of mechanical agitation and may require proteolytic enzymes. High gradient magnetic cell separation (MACS) can enrich cell populations by greater than 100-fold. Magnetic microparticles (<80 nm), which remain attached to the positive cell population, do not interfere with proliferation assays or flow cytometry. Affinity methods offer the selectivity of monoclonal antibody based separations and are required for large-scale clinical applications.

Large-scale affinity separation techniques (>$10^9$ cells) have played an important role in the development of bone marrow transplant and adoptive cellular immunotherapy. If there is homogeneous expression of tumour markers, then magnetic bead absorption can purge tumour cells from autologous grafts. Enrichment strategies are useful for the purification of autologous haemopoietic progenitor cells using the CD34 marker or collection of lymphoid subsets for adoptive immunotherapy. About 1% of a bone marrow graft is CD34 positive. Purities of CD34 positive cells exceeding 90% require greater than 900-fold enrichment factors. Work has therefore concentrated on improving the efficiency of cell enrichment using affinity cell separation.

A method for the separation of cells from a mixed population of cells has been reported by Bigalow et al 1989, Journal of Immunological Methods 117: 289–293. These authors have reported the development of a hybrid of two separation methods, cellular adhesion chromatography (AC) and field-flow fractionation (FFF) that achieves effective separation of rat mesenteric B and T lymphocytes. This method combines the selective adhesion of AC and the control displacement forces of FFF, it also yields quantitative estimates of the binding forces of B and T lymphocytes to the adhesion surface of the system. This method uses an apparatus comprising two parallel glass plates and utilises the different binding affinities to these plates by different cell types. This method has a major problem in that it utilises the inherent binding properties of cells to the particular glass surfaces and that it cannot be scaled up to separate a large number of cells.

The present inventors have developed a method for the separation of a desired cell type from a population of cells that has the ability to select any given cell type and also may be scaled up for use in clinical applications.

DISCLOSURE OF INVENTION

Accordingly, in a first aspect the present invention consists in a method for removing a desired cell type from a sample containing cells including the desired cell type, the method comprising the steps of:

(a) loading the sample into a device including a semi-permeable substrate provided with a ligand reactive with the desired cell type, (b) incubating to allow deposition and binding of the desired cell type to the ligand, (c) treating the semi-permeable substrate in a manner such that the cells not bound to the ligand are removed, and optionally (d) treating the semi-permeable substrate in a manner such that the cells bound to the ligand are removed.

In a preferred embodiment of the first aspect, the semi-permeable substrate is cellulose and is in the form of a hollow fibre(s). Where the semi-permeable substrate is in the form of hollow fibres in order to obtain the optimum separation of any given cell type, it is preferred that the permeability of the substrate is such that the fluid loss across the substrate is less than 5%.

Other types of hollow fibres may also be used including ultrafiltration hollow fibre membranes made of polyamide. When such ultrafiltration membranes are used it will typically be necessary to use the membranes under conditions such that the permeability of the membrane is reduced below its normal level.

In a further preferred embodiment of the first aspect, the ligand is selected from the group consisting of an antibody, lectin, growth factor and receptor. More preferably, the ligand is an antibody and still more preferably the antibody is a monoclonal antibody.

In a further preferred embodiment of the present invention the treatment in steps (c) and (d) comprises shear stress. The cells not bound to the semi-permeable substrate are removed by low shear stress and cells bound to the semi-permeable substrate are removed by higher shear stress. After removal of the unbound cells, the cells bound to the semi-permeable substrate may be pre-treated with a cell-releasing agent prior to removal by treatment with shear stress. Preferably the cell-releasing agent is an enzyme and more preferably and enzyme is chymopapain. If the bound cells are pre-treated, then the shear stress used to remove the pre-treated bound cells may be lower, the same or higher than the shear stress used to remove the unbound cells.

In the preferred embodiment where the semi-permeable substrate is in the form of a hollow fibre, the treatment to remove the cells is by shear stress generated by the flow of liquid through the hollow fibre. Shear stress may be generated by increasing the flow of fluid through the fibre or by increasing the viscosity of the fluid or by utilising a mixture of both procedures.

In this form, the cells that are not bound to the semi-permeable substrate are eluted by low shear stress and the cells bound to the semi-permeable substrate are eluted by high shear stress. Alternatively, the cells not bound to the semi-permeable substrate are removed by low shear stress and the cells bound to the semi-permeable substrate are pre-treated with a cell-releasing agent prior to removal by treatment with shear stress. Preferably the cell-releasing agent is an enzyme and more preferably the enzyme is chymopapain. The shear stress used to remove the pre-treated bound cells may be lower, the same or higher than the shear stress used to remove the unbound cells.

In yet a further preferred embodiment of the first aspect of the present invention the method includes growing the desired cells in the device after separation. In this embodiment after step (c) the bound cells are maintained under conditions in which the cells may divide and multiply.

In a second aspect, the present invention consists in an apparatus for removing a desired cell type from a sample including the desired cell type comprising a semi-permeable substrate in the form of an array of hollow fibres provided internally with a ligand reactive to the desired cell type.

In a preferred embodiment of the second aspect, the ligand is selected from-the group consisting of antibody, lectin, growth factor and receptor. More preferably, the ligand is an antibody and still more preferably the antibody is a monoclonal antibody.

In a further preferred embodiment of the second aspect, the hollow fibres are cellulose and the fluid loss across the wall of the hollow fibre is less than 5%.

Other types of hollow fibres may also be used including ultrafiltration hollow fibre membranes made of polyamide. When such ultrafiltration membranes are used it will typically be necessary to use the membranes under conditions such that the permeability of the membrane is reduced below its normal level.

In a still further preferred embodiment of the second aspect, the hollow fibres are held within a cylindrical module. The module contains ports to allow buffer to be circulated around the outside of the fibres and also inlet and outlet ports to allow flow through the fibres. This arrangement of the hollow fibres allows the inside to be sealed from the outside so that flow along the inside of the fibre can be controlled independently from the flux across the walls of the fibre. The fluid flow to the hollow fibre module is preferably achieved by a pump means.

In further aspects the present invention consists in cells obtained using the method of the first aspect of the present invention or the apparatus of the second aspect of the present invention.

In order that the nature of the present invention may be more clearly understood, preferred forms thereof will be described with reference to the following examples and drawings.

BEST MODES FOR CARRYING OUT THE INVENTION

Figure 1:
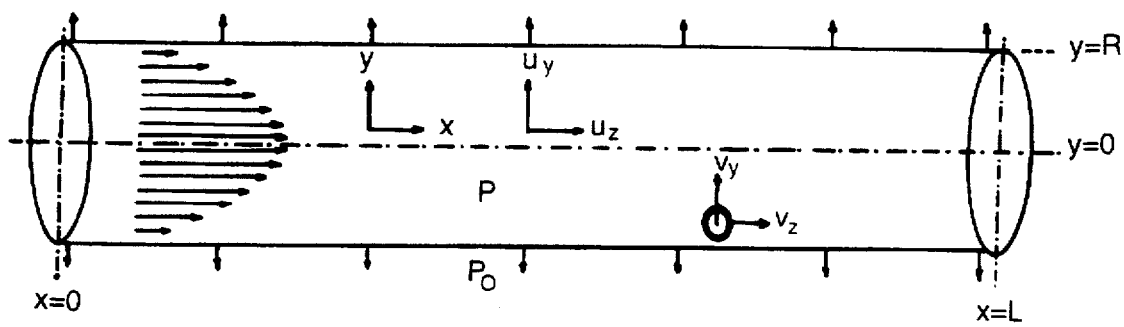
FIG. 1 shows a schematic representation of laminar flow observed in a porous tube.

The present inventors have utilised mathematical modelling to determine the preferred permeability requirements of the semi-permeable substrates that may be best used in the invention. In particular, the permeability of hollow fibres has been calculated to ensure efficient cell deposition and recovery.

DEPOSITION OF CELLS WITHIN PERMEABLE HOLLOW-FIBRE MODULES AND RECOVERY USING UNIFORM SHEER STRESS

The permeable hollow-fibre separation process may be divided into 3 stages:

1. Cell deposition within the device using either closed-ended filtration or open-ended flow.
2. Elution of marker negative populations at low shear stress (open-ended flow).
3. Elution of adherent populations (marker positive) at higher shear stress (open-ended flow).

Very low flow rates are required for cell-deposition using open-ended flow. Closed-ended filtration has the advantage of higher volume flow rates, and more complete capture of cells by the device. Hydraulic permeability must be carefully selected so that adequate volume flow rates may be generated using closed-ended filtration during the cell deposition phase (stage 1), as well as generating uniform shear stress during the open-ended flow cell recovery phase (stages 2 and 3).

Comparison of open-ended and closed-ended flow for cell deposition

For open-ended flow the outlet of the hollow-fibre array is open to atmospheric pressure. Cells will pass directly through the hollow-fibre system and may attach to the walls of the fibres if the shear stress is very low (<0.2 dynes/cm$^2$). A 1 m$^2$ device has 8000 fibres (inner fibre diameter 200 μm, length 20 cm) in parallel. The wall shear stress may be calculated using the Poiseuille-Hagen law for laminar tube flow.

$$\tau = \frac{4Q\mu}{n\pi r^3}$$

where Q is the flow-rate, μ the fluid viscosity, the tube radius, and n the number of fibres in the parallel array. Using the dimensions of a 1 m² device, flows less than 0.1 ml/sec are required for cell deposition. For processing of clinical samples such as blood apheresis collections (>200 ml), the deposition process will be time consuming (>30 minutes).

It is possible to generate larger fluxes for cell deposition if the fibres are permeable to water and the end of the hollow-fibre array is sealed using a stop flow valve. A "Bioflux" Cuprophan membrane (supplied by AKZO FASER AG, Obernburg, Germany, 63785) has a hydraulic flux of greater than 50 ml/(min.m².100 mmHg). A volume of 200 ml could be deposited within a device within 2 minutes (filtration pressure=200 mmHg).

Selection of hollow-fibre hydraulic permeability for uniform shear elution

The selection of fibre hydraulic permeabilities for uniform shear elution affinity cell separation will be a compromise. Highly permeable fibres may be used for rapid loading of cells using closed-ended filtration. If the fibre is too permeable, then during open-ended mode and cell recovery, the net radial flux will result in a drop in axial flow and surface shear stress along the fibre. Non-uniform shear stress will result in reduced separation purity and recovery.

Set out below is a summary of the derivation of the velocity field for a porous hollow tube (1). This may be used to calculate the fluid losses across the fibre membrane for open-ended filtration. For fluid losses across the membrane to be less than 5%, then $$MX_L < 0.3$$

where M is the non-dimensional hydraulic permeability and $X_L$ is the non-dimensional fibre length.

For large-scale hollow-fibre module dimensions (fibre inner radius=100 μm, fibre length=20 cm), the hydraulic permeability should be less than $1.4 \times 10^{-11}$ cm. Typical Cuprophan dialysis membranes have a hydraulic permeability of about $1.5 \times 10^{-12}$ cm, well below the maximum hydraulic permeability required for uniform shear elution (<5% drop along fibre). Whilst these membranes are suitable for uniform shear elution using open-ended flow, rapid loading of cells is not possible using blind ended filtration. The high flux Cuprophan membrane "bioflux" is more suitable for this purpose (hydraulic permeability $>6.4 \times 10^{-12}$ cm). Such a membrane can generate filtration flows of >50 ml.min⁻¹.m⁻². 100 mmHg and will generate uniform shear stress along the fibre length (<5% drop) during open ended flow.

VELOCITY FIELD FOR A POROUS HOLLOW TUBE

The solution of the Navier-Stokes equation for laminar flow in a porous tube has been derived by Granger and coworkers (1). The flow-field may be used to derive trajectories for particles which follow streamlines. Diffusion, sedimentation and inertial effects will result in deviation away from this purely convective model.

The undisturbed velocity flow-field U is derived by applying the Navier-Stokes equations. Symmetry results in simplifying the problem to that of two dimensions where axial and radial velocities ($u_x$, $u_y$) (vary with axial and radial position (x,y) (see FIG. 1). Pressure p forms a scalar field inside the tube, whilst $p_o$, the pressure outside the tube, is constant.

Boundary conditions are assumed to be as follows: Radial fluid velocity across the wall of the tube radius R is given by Darcy's Law.

$$u_{y(y=R)} = \frac{k}{\mu} (p_{(y=R)} - p_o) \qquad A4.1$$

where k is the hydraulic permeability and μ the viscosity of the fluid.

Furthermore it is assumed that there are "no slip" conditions at the walls ($u_{x(y=R)}=0$). The radial velocity at the centre of the tube is zero ($u_{x(y=R)}=0$). Tube hydrodynamic end-effects are neglected.

The Navier-Stokes equations using cylindrical coordinates simplifies to $$x\text{-momentum } \rho \left( u_x \frac{\partial u_x}{\partial x} + u_y \frac{\partial u_x}{\partial y} \right) = \qquad A4.1$$

$$-\frac{\partial p}{\partial x} + \mu \left\{ \frac{1}{y} \frac{\partial}{\partial y} \left( y \frac{\partial u_x}{\partial y} \right) + \frac{\partial^2 u_x}{\partial x^2} \right\}$$

$$y\text{-momentum } \rho \left( u_x \frac{\partial u_x}{\partial x} + u_y \frac{\partial u_y}{\partial y} \right) =$$

$$-\frac{\partial p}{\partial y} + \mu \left\{ \frac{\partial}{\partial y} \left( \frac{1}{y} \frac{\partial}{\partial y} (yu_y) \right) + \frac{\partial^2 u_y}{\partial x^2} \right\}$$

$$\text{continuity } \frac{\partial u_x}{\partial x} + \frac{1}{y} \frac{\partial}{\partial y} (yu_y) = 0$$

where ρ is the fluid density and μ the fluid viscosity.

The mathematical formulation is simplified with non-dimensional variables:

$$X = \frac{x}{R} \; ; X_L = \frac{L}{R} \; ; Y = \frac{y}{R} \; ; T = \frac{\overline{u}_{x(x=0)}}{R} t \qquad A4.3$$

$$\overline{U}_x = \frac{\overline{u}_x}{\overline{u}_{x(x=0)}} \; ; \overline{U}_L = \frac{\overline{u}_{x(x=L)}}{\overline{u}_{x(x=0)}} \; ; U_y = \frac{\overline{u}_y}{\overline{u}_{x(x=0)}} \; ; P = \frac{p - p_o}{p_o}$$

$$M = 4 \sqrt{\frac{k}{R}} \; ; Re = \frac{2\rho \overline{u}_{x(x=0)} R}{\mu}$$

where t is time.

Granger obtained an iterative solution by first assuming that the velocity profile is parabolic, and then using the expression for $U_x$ to obtain a first iteration for $U_y$ from the continuity equation. Expressions for P were found using the Y-momentum equation. A new expression for $U_x$ was derived using the X-momentum expression and then reintroduced into the continuity equation and so on iteratively. What results is a development in M, the coefficients of which are polynomials in Y.

$$U_x = 2K(1 - Y^2) + \frac{MKGRe}{72} (29 - 36Y^2 + 9Y^4 - 2Y^6) + \qquad A4.4$$

$$\frac{KM^2}{8} (3 - 4Y^2 + Y^4) +$$

$$\frac{M^3KGRe}{4608} (119 - 96Y^2 - 36Y^4 + 16Y^6 - 3Y^8) + \ldots$$

$$U_y = \qquad A4.5$$

$$\frac{MG}{2} (2Y - Y^3) + \frac{M^2Re}{288} (K^2 + G^2)(58Y - 36Y^3 + 6Y^5 - Y^7) +$$

$$\frac{M^3G}{48} (9Y - 6Y^3 + Y^5) + \ldots$$

where G=—(B cosh MX+sinh MX), K=cosh MX+B sinh MX, and $$B = \frac{\overline{U}_L - \cosh MX_L}{\sinh MX_L}.$$

Microfiltration and ultrafiltration membranes have hydraulic permeabilities which range from $10^{-8}$ cm$<$k$<10^{-12}$ cm. M is relatively small and only the first term of each development is significant.

$$U = 2K(1 - Y^2)i + \frac{MG}{2}(2Y - Y^3)j \qquad \text{A4.6}$$

where U is the flow velocity vector; i and j are unit vectors in the X and Y direction.

A particle which follows streamlines will have the same velocity vector V as the flow-field.

$$U = V = \frac{dX}{dT}i + \frac{dY}{dT}j \qquad \text{A4.7}$$

Substitution of equation A4.6 into A4.7 gives $$dT = \frac{dX}{2K(1-Y^2)} = \frac{2dY}{MG(2Y-Y^3)} \qquad \text{A4/8}$$

Separation of variables and integration gives the trajectory equation in K and Y.

$$K = \frac{c}{Y^2(2-Y^2)} \qquad \text{A4.9}$$

where $c = K_p Y_p^2 (2 - Y_p^2)$ and $(K_p(X_p), Y_p)$ is a point on the trajectory.

Figure 2:
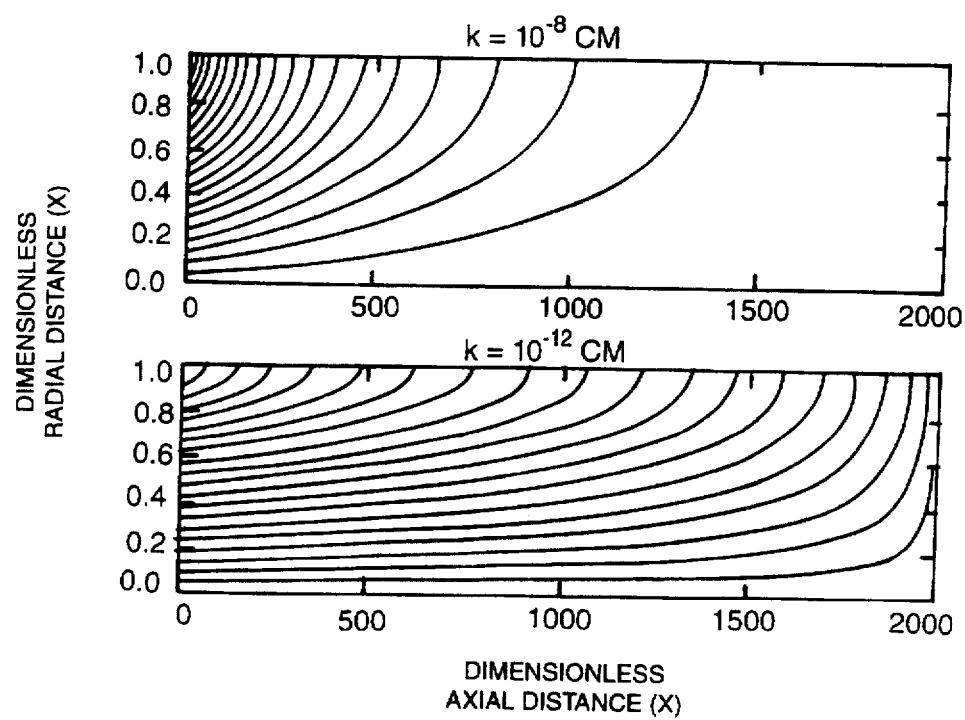
FIG. 2 shows the streamlines determined for laminar flow in a porous tube.

FIG. 2 shows the streamline pattern for low (k=$10^{-12}$ cm) and high (k=$10^{-8}$ cm) permeability membranes with $\overline{U}_L=0$ (blind-ended filtration). Streamlines are more closely spaced proximally for a highly permeable fibre. An important result of this model is the effect of permeability on the transmembrane fluid flux along the length of the tube. If the fibre has high permeability, then the drop in pressure along the tube due to viscous flow is enough to drive a greater transmembrane flux proximally.

SELECTION OF FIBRE PERMEABILITY FOR UNIFORM SHEAR ELUTION

For cell recovery, the end of the porous tube is open to the outside pressure, $p_o$. Even though the end of the tube is open, there will be a pressure gradient along the tube (due to viscous resistance), and this will drive filtration (open-ended filtration).

Therefore the selection of fibre hydraulic permeabilities for uniform shear elution affinity cell separation will be a compromise. For cell deposition using blind-ended filtration, cells may be rapidly loaded into fibres which have a high hydraulic permeability. On the other hand, for cell recovery (open-ended filtration), high fibre permeability will result in a significant drop in axial flow along the fibre with a drop in fluid surface shear stress.

Granger et al (1) derives an expression for the non-dimensional mean pressure $\overline{P}$ as a function of non-dimensional axial distance X.

$$\overline{P} = \frac{-\mu u_{(x=0)}}{k p_o} M(\sinh MX + B\cosh MX) \qquad \text{A4.10}$$

where $\overline{P} = \frac{\overline{p} - p_o}{p_o}$.

If there is open ended flow, then $\overline{p}=p_o$ at x=L. The mean non-dimensional fractional outflow velocity $\overline{U}_L$ can be calculated from B with $\overline{P}=0$ at $X_L$.

$0 \sinh MX_L + B \cosh MX_L$;

$$\overline{U}_L = \frac{\cosh^2 MX_L - \sinh^2 MX_L}{\cosh MX_L}; \qquad \text{A4.11}$$

$\overline{U}_L = 1/\cosh MX_L$

For the fluid losses across the membrane to be less than 5% ($\overline{U}_L > 0.95$), then $$MX_L < 0.3 \qquad \text{A4.12}$$

For typical hollow-fibre module dimensions (R=100 μm, L=20 cm) k$<1.4 \times 10^{-11}$ cm. A typical cuprophan dialysis membrane has a k=$1.5 \times 10^{-12}$ cm. A suitable membrane would have a hydraulic permeability about 10-fold greater than dialysis cuprophan.

1. Granger J, Dodds J, Midoux N. Laminar flow in Channels with Porous Walls. *The Chemical Engineering Journal*. 1989; 42:193–204.

THE USE OF ULTRAFILTRATION HOLLOW FIBRE MEMBRANES FOR UNIFORM SHEAR ELUTION AFFINITY CELL SEPARATION

For cell fractionation using uniform shear stress, there must be uniform axial flow rate along the fibre length. The preceding discussion defines a permeability below which there is minimal leak across the fibre membrane. Whilst ultrafiltration membranes have a permeability well above this value, a process will be described whereby membrane pores may be temporarily sealed for uniform shear elution.

The separation process is as follows:

1. Loading of cells using blind-ended filtration.
2. Drainage of fluid surrounding hollow fibres (extra-capillary space).
3. Application of extra-capillary gas pressure greater than intracapillary pressure and less than the bubble point or collapsing pressure of the fibre. Membrane pores are sealed by formation of a gas-water interface. Surface tension prevents gas from entering the fibre lumen.
4. Recovery of cells not bound to the ligand by treating with low shear stress.
5. Recovery of cells bound to the ligand by treating with higher shear stress.

The technique for sealing membrane pores using an extra capillary gas pressure and a gas-water interface seal, has been demonstrated using nylon microporous hollow fibre modules. Table 1 gives the relevant specifications for this fibre type (supplied by AKZO Fazer, Fibres division, Wuppertal, Germany).

TABLE 1

| Capillary Membrane PA-386c | |
| --- | --- |
| Polymer | polyamide |
| Inner diameter | 300 ± 10 μm |
| Wall thickness | 110 ± 10 μm |
| Maximum pore size | <0.43 ± 10 μm |
| Hydraulic permeability (25C) | 2.2 × 10$^{-9}$ cm |
| Implosion pressure | >10$^5$ Pa |
| Bubble point | >3.2 × 10$^5$ Pa |

Without application of extracapillary gas pressure, flow along this fibre results in significant leakage of fluid across the membrane (hydraulic permeability >1.4×10$^{-11}$ cm). Application of 50 kPa gas pressure to the extra-capillary space prevented leakage of fluid across the membrane. This pressure is well below the bubble point and collapsing pressure of this hollow-fibre membrane.

Flow from the intra to extra-capillary space is prevented by a positive pressure in the extra-capillary space. Flow from the extra-capillary space into the intra-capillary space will cease as soon as a gas-liquid interface forms at the membrane pore entrance. Surface tension prevents gas from entering the fibre.

The pressure drop inside the tube due to viscous flow may be calculated from the Hagen-Poiseuille law:

$$\Delta p = 2\tau \frac{L}{R}$$

where Δp is the pressure drop, is the wall shear stress, L is the tube length, and R is the tube radius. Therefore, flow generating 100 dynes/cm$^2$ (sufficient for cell recovery) will result in a pressure drop of 25 kPa along a 20 cm fibre. This is below the applied extra-capillary gas pressure (50 kPa), the bubble point (320 kPa) and collapsing pressure (100 kPa) of this fibre type.

In summary, ultrafiltration membrane pores may be sealed using a gas-fluid interface provided:

1. Gas on the outside of the hollow fibre, fluid on the inside.
2. Extra-capillary gas pressure is greater than the intra-capillary pressure.
3. The bubble point of the fibre is less than the extra-capillary gas pressure.
4. Extra-capillary gas pressure is less than the collapsing pressure of the hollow fibre.

SEPARATION OF NALM-6 CELLS FROM CEM CELLS

A positive cell population was formed by coating NALM-6 cells with a mouse monoclonal antibody by incubating the cells with the anti-CD9 antibody FMC56. Negative cells were CEM cells prestained with the nuclear fluorescent stain H33342 so that they could be distinguished from the positive cells by UV fluorescence. Equal numbers of the negative and positive cells were mixed before separation.

A cellulose hollow fibre cell separation module was constructed by coupling polyclonal antibody (raised in sheep) against mouse immunoglobulin to the inner surface of the hollow fibres using periodate reaction. The coupling reaction was carried out by activation of the cellulose hollow fibres with 0.5M sodium periodate for two hours at room temperature and then binding the polyclonal antimouse IgG antibody at 200 μg/ml overnight at 4° C. The hollow fibre module was then washed with buffer to remove unbound antibody and all traces of the coupling chemicals.

The cells were loaded into the hollow fibres by applying a 20 μl drop of cell suspension to the open end of the module. The cells were drawn into the fibre lumen under the action of gravity and surface tension prevented air from entering the fibres. The header port was replaced and closed and the device was rotated to a horizontal position to facilitate contact between the cells and the inner surface of the fibres. The cell sediment under gravity at about 4 μm-sec so that full deposition was completed in 60 seconds. Attachment kinetics were rapid and 4 minutes was long enough for the completion of binding. The device was rotated a further 90° (inverted) the negative cells were fractionated from positive cells using shear stress (proportional to flow rate). A flow rate of 2.5 ml per minute (1.5 DYNES/cm$^2$) was sufficient to remove most of the negative cells from the device. A flow greater than 50 ml per minute (30 DYNES/cm$^2$) was sufficient to recover all of the bound positive cells.

FIG. 2 shows absolute numbers of positive and negative cells eluted from successive fractions. Fraction 0 shows a total number of positive and negative cells eluted from the device and has a similar ratio to the initial mix. All of the cells applied to the device were recovered using flow elution. Most of the negative cells (filled bar) and some positive cells were eluted in fraction 1 at low shears (2.5 ml per minute). Fractions 2–6 have relatively few cells and the remaining bound positive cells were recovered in fraction 7 where higher flow rates (greater than 50 ml per minute) were applied. Approximately 70% of the positive cells were recovered in this fraction. This fraction was 99.7% pure. Removal of the header and drop wise elution of cells from the inverted device dramatically reduced flow dispersion with substantial improvements enrichment purity.

Figure 3:
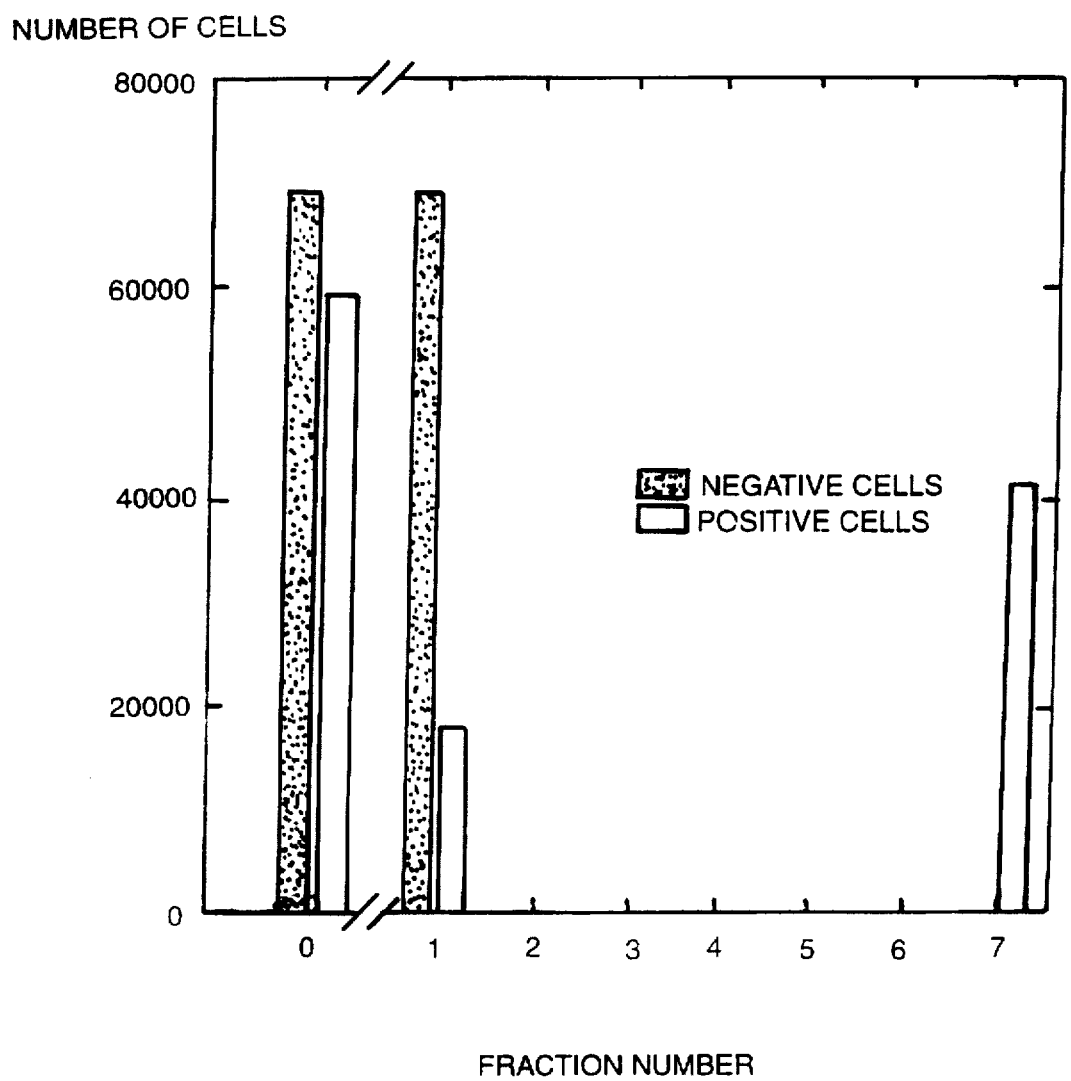
FIG. 3 shows the results of the fractionation of cells using an apparatus of the present invention.
Figure 4:
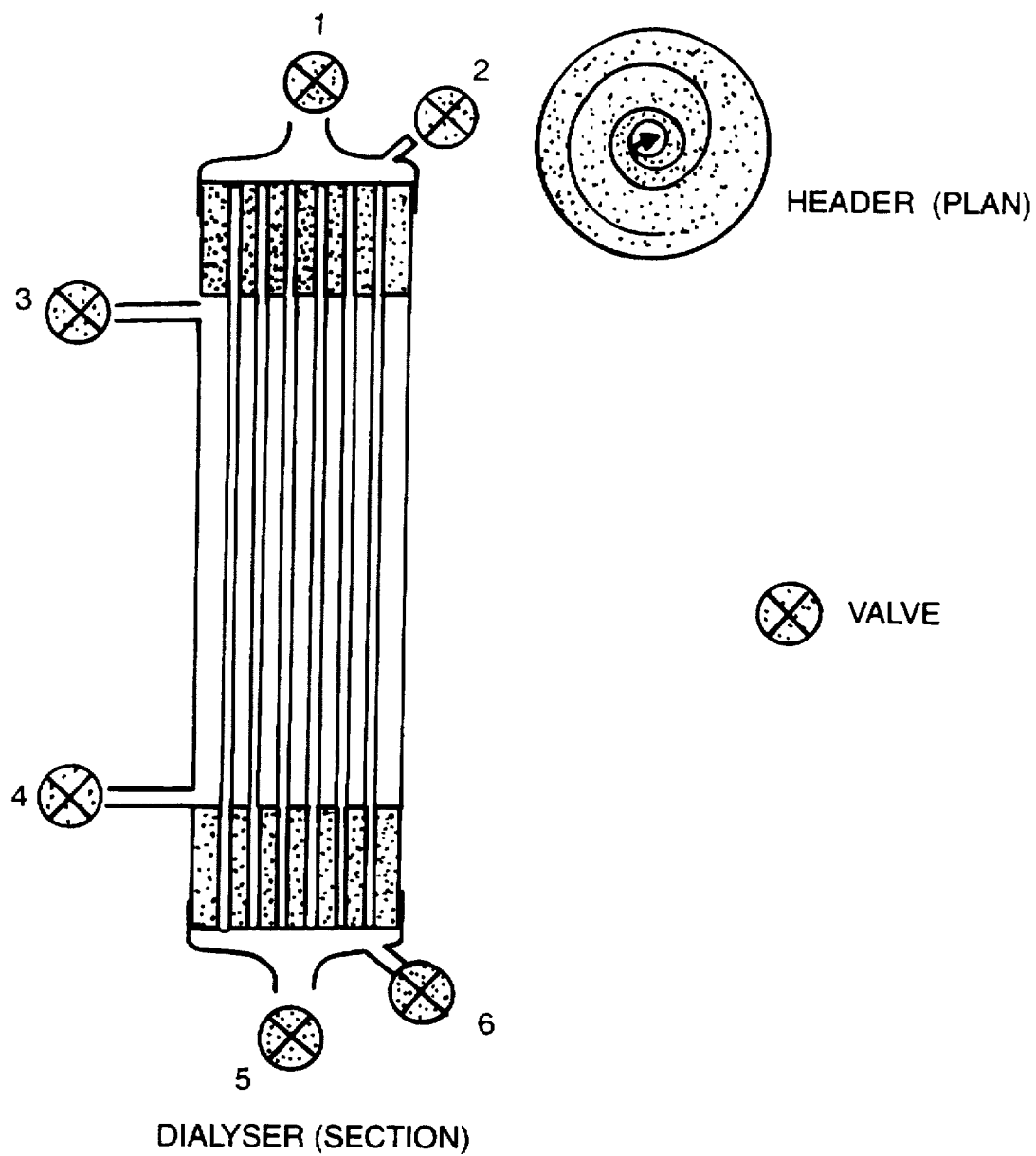
FIG. 4 shows a schematic representation of an apparatus of the present invention indicating the valve numbering as referred to in Table 2.

A schematic representation of the apparatus for removing a desired cell type from a sample containing a mixed cell population including the desired cell type is given in FIG. 3. The apparatus can be operated in a batch mode as summarized in Table 2.

TABLE 2

| Flow control system for cell separation device. | | | | | | | |
| --- | --- | --- | --- | --- | --- | --- | --- |
| Phase | Valve 1 | Valve 2 | Valve 3 | Valve 4 | Valve 5 | Valve 6 | Flow |
| Cell loading | Open | Closed | Closed | Open | Closed | Closed | 1 to 4 |
| Inlet header flus | Open | Open | Closed | Closed | Closed | Closed | 2 to 1 |
| Adhesion | Closed | Closed | Closed | Closed | Closed | Closed | Nill |
| Recovery of negative cells | Open | Closed | Closed | Closed | Open | Closed | 1 to 5 Low flows |
| Outlet header flush | Closed | Closed | Closed | Closed | Open | Open | 6 to 5 |
| Recovery of positive cells | Open | Closed | Closed | Closed | Open | Closed | 1 to 5 High flows |

Cells are loaded using blind ended filtration (flow from valve 1 to 4). Most of the cell population is concentrated within the hollow fibres. The inlet vortex header is flushed (flow from valve 2 to 1). All valves are closed for cell deposition and adhesion (device in horizontal position). The negative cell population is eluted at low shear (flow from valve 1 to 5). Residual negative cells are flushed from the outlet vortex header (flow from valve 6 to 5). Finally the positive cell population is recovered using high shear (flow from valve 1 to 5).

The vortex headers prevent contamination of purified negative and positive cell populations. The loading of cells into the hollow fibre module using blind ended filtration minimizes cell losses in the header space.

As will be appreciated the present invention provides a novel process of the separation of cells. The method of the present invention is believed to provide an easier and highly selective method of cell separation than that of the techniques currently in use. The present invention also is adaptive for automation and large scale production of given cell populations by a device similar in configuration to a hollow fibre hemodialyser.

APPLICATION OF HOLLOW-FIBRE CELL SEPARATION DEVICE TO CELL EXPANSION CULTURE SYSTEMS

Instead of recovering the selectively adsorbed cell population, cells which have been adsorbed to the lumenal surface of the hollow fibre may be left in situ, and allowed to proliferate. The hollow-fibre membrane will be permeable to growth factors and metabolites, so that the cells may be supported by perfusing culture media around the outside of the fibres. Once cells have grown to optimal density, they may be harvested by fluid flow along the lumen of the fibres.

Cells will consume anabolites (e.g., oxygen, glucose, amino acids), and produce catabolites (lactate, $CO_2$, $H^+$). In addition cells will consume growth factors, and produce inhibitory factors. Thus for maximal growth, the culture media must be continually replaced with fresh media. Hollow-fibre perfusion systems may be used to continually exchange components of this culture medium.

Figure 5:
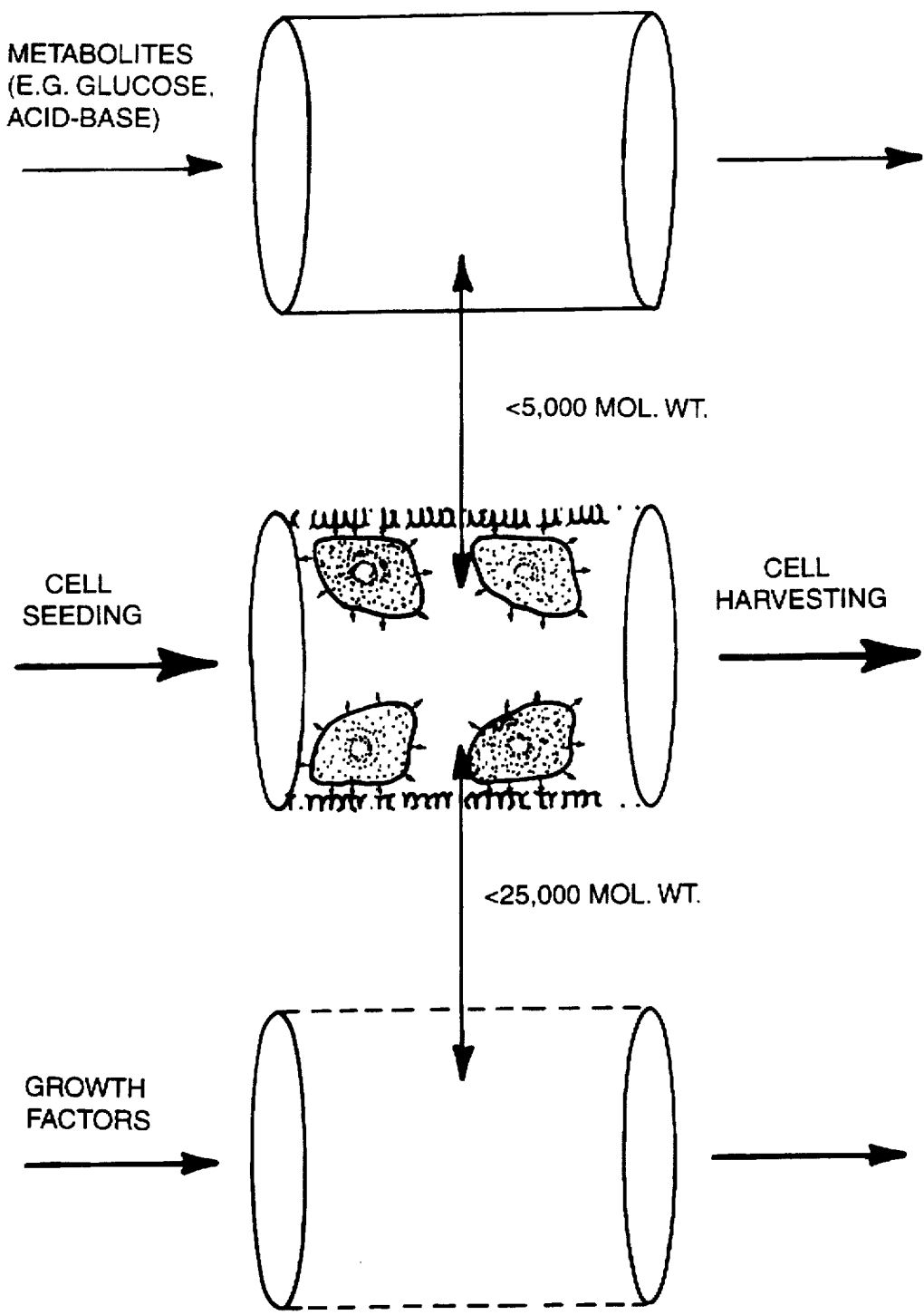
FIG. 5 is a schematic representation of cell selection and subsequent expansion of the cells using a hollow fibre apparatus of the present invention.

Low molecular weight substance (<5,000) are involved in the metabolism of the cell (e.g., glucose, amino acids, $O_2$, $CO_2$, $H^+$, lactate etc.) are consumed and produced at a greater rate than larger molecular weight substance such as growth and inhibitory factors (molecular weight 5,000–25,000). The low molecular weight fraction may be exchanged using dialysis membranes (impermeable to molecules with a molecular weight >5,000). The fraction containing growth factors may be exchanged independently of the former using semi-permeable membranes with a higher molecular weight cut-off. FIG. 5 shows a schematic representation of a system which combines hollow-fibre cell selection and expansion.

This system has the application for the development of cell therapies which involve cell selection and expansion culture. For example, the duration of life threatening pancytopenia associated with conventional bone marrow transplant (2–3 weeks) could be shortened to a few days by administration of granulocyte and platelet precursors derived from bone marrow stem cells. Haemopoietic stem cells may be isolated using antibody to CD34 (stem cell marker). These cells may be expanded and matured in culture to produce granulocyte and platelet precursors. Both primitive haemopoietic cells and more mature precursors would be given immediately after myeloablative chemoradiotherapy for cancerl resulting in short and long term regeneration of haemopoiesis.

SEPARATION OF CD34$^\pm$ CELLS

Antibody coupling chemistry

A method for antibody oxidation, and the derivatisation of Cuprophan hollow-fibre modules with adipic dihydrazide has been used to couple the antiCD34 monoclonal antibodies, #9069 (clone 9 C5) or #9079 (clone HPCA-2), to Cuprophan hollow-fibre modules. Hydrazide derivatisation of Cuprophan modules Blind-ended filtration was used to deposit cells within modules and therefore the antibody coupling process should not significantly reduce the hydraulic permeability of Cuprophan modules.

Heat annealing of modules was required to prevent alkali-induced stress cracking of polycarbonate module shells. Dehydration of Cuprophan membrane was associated with a significant drop in hydraulic permeability (see Table 3). Therefore polycarbonate modules were heat annealed in the hydrated state by autoclaving them in water for 20 minutes at 121° C.

The reaction with 50% ethylene glycol diglycidyl ether (EGDGE) also resulted in a significant decline in hydraulic permeability (see Table 3). The level of cross-linking was reduced by lowering the concentration of EGDGE (10%).

TABLE 3

The effect of dehydration and cross-linking of Cuprophan hydraulic permeability

| Process | Hydraulic permeability (ml/min/100 mm Hg/m$^2$) | Percentage of initial value |
|---|---|---|
| Unmodified (Cuprophan F1) | 52 | 100 |
| Dry autoclaving | 1.6 | 31 |
| Wet autoclaving | 4.3 | 83 |
| 50% EGDGE (after wet autoclaving) | 0.67 | 16 |
| 10% EGDGE + Adipic dihydrazide | 3 | 58 |

Method

Modules were heat annealed fully hydrated in an autoclave (121° C. for 20 minutes) prior to reaction with a 10% solution of EGDGE. After extensive washing of Cuprophan modules in distilled water, 20 ml of the EGDGE solution is recirculated (5 ml/min) through Cuprophan hollow fibre modules immersed in a 50° C. water bath for one hour. The modules were then washed thoroughly with distilled water. 20 ml of filtered 10% adipic dihydrazide is recirculated at 1 ml/min overnight. The next day the module is washed and stored in PBS (phosphate buffered saline) +0.1% Na Azide.

Antibody oxidation and coupling to modules

Antibody carbohydrate moieties were oxidised using sodium periodate. Oxidised antibody solution was recirculated through hydrazide derivatised modules overnight at room temperature, or over the weekend at 4° C. The two different oxidation and coupling protocols are shown below:

Method 1

Antibody solution (0.5–2 mg Ig) is desalted against 0.2M sodium acetate buffer pH 5.0 using a PD10 column (Pharmacia). 40 µl of 1M NaIO$_4$ solution is added to 2 ml of antibody solution to make a final concentration of 20 mM NaIO$_4$. Antibody is oxidised at 4° C. for 1 hour in the dark with gentle agitation. The reaction is quenched with glycerol (final concentration 15 mM). The quenched solution is immediately desalted against sodium acetate buffer. The optical density at 280 nm of the oxidised antibody solution is measured, and 6 ml recirculated (e 200 µl/min) through the bore of hydrazide derivatised modules over the weekend at 4° C. The optical density of the oxidation solution is measured again after completion of coupling. Modules are washed and stored in PBS+0.1% Na azide at 4° C.

Method 2

Antibody is oxidised for 1 hour at room temperature in the dark. 20 µl of 1M NaIO$_4$ concentration of 10 mM. After quenching, the solution is desalted against 0.1M acetate buffer (pH 4.5), and recirculated overnight through the bore of hydrazide derivatised modules are room temperature.

Flow protocols for cell separation

A microcomputer controlled system was used to generate flow for shear fractionation of cell populations. The flow protocol file is read by software which generates stepper motor speeds and screen instructions for separation experiments. Table 4 shows the separation protocol which was used in subsequent experiments.

With the module in the vertical position, cells are injected slowly into the outlet port of the hollow fibre module (~2.5 ml in 4 minutes), with the inlet valve closed (blind-ended filtration). About two void volumes is sufficient to fill the module with cells resulting in an even distribution of cells along the module length, with no cells in the inlet header, and relatively few cells in the outlet header.

The module is then rotated into the horizontal position for cell sedimentation and attachment. Deposition distances are less than 200 μm (deposition time <60 seconds), and after a period of 120 seconds, the module is slowly rotated along its long axis (90° increments every 120 seconds). This creates a probability of cell attachment along the entire inner circumference of fibres. After incubation with the membrane surface, the module is returned to the vertical position, and 10 ml cell fractions are sequentially eluted, with flow-rate incremented to a higher value for each subsequent fraction.

TABLE 4

Flow protocol for cell separation

| Action | Duration (seconds) |
|---|---|
| 10 ml module flush | 10.24 |
| Refill feed syringe (10 ml) | 25.61 |
| Draw up 2 ml of cell suspension | 20.49 |
| Inject 2.4 ml from cell syringe | 204.89 |
| Deposition of cells (module horizontal) | 120 |
| Rotate 90 degrees | |
| Deposition of cells (120 seconds) | 120 |
| Rotate 90 degrees | |
| Deposition of cells (120 seconds) | 120 |
| Rotate 90 degrees | |
| 10 ml fraction at 1 dyne/cm² | 512.22 |
| Refill feed syringe (10 ml) | 25.61 |
| 10 ml fraction at 2 dyne/cm² | 256.11 |
| Refill feed syringe (10 ml) | 25.61 |
| 10 ml fraction at 5 dyne/cm² | 102.44 |
| Refill feed syringe (10 ml) | 25.61 |
| 10 ml fraction at 10 dyne/cm² | 51.22 |
| Refill feed syringe (10 ml) | 25.61 |
| 10 ml fraction at 25 dyne/cm² | 20.49 |
| Refill feed syringe (10 ml) | 25.61 |
| 10 ml fraction at 50 dyne/cm² | 10.24 |
| Refill feed syringe (10 ml) | 25.61 |
| 10 ml fraction at 75 dyne/cm² | 6.83 |
| Refill feed syringe (10 ml) | 25.61 |
| 10 ml fraction at 100 dyne/cm² | 5.12 |
| Refill feed syringe (10 ml) | 25.61 |
| 10 ml fraction at 150 dyne/cm² | 3.41 |
| Refill feed syringe (10 ml) | 25.61 |
| 10 ml fraction at 200 dyne/cm² | 2.56 |

The hollow fibre wall shear stress $\tau$ is calculated using:

$$\tau = \frac{4Q\mu}{n\pi r^3}$$

where $Q$ is the device flow-rate, $\mu$, the fluid viscosity, $n$, the number of fibres per device and $r$ the fibre internal radius. The dimensions of the modules used are shown in Table 5.

The elution shear stresses for this flow protocol were 1, 2, 5, 10, 25, 50, 75, 100, 150, 200 dynes/cm²

TABLE 5

Device dimensions

| Fibre type | Cuprophan F1 (dialysis membrane) |
|---|---|
| Inner fibre radius (r) | 100 μm |
| Number of fibres | 348 |
| Fibre length | 20 cm |
| Lumenal void volume | 2.2 ml |
| Lumenal surface area | 437 cm² |
| viscosity (PBS + 0.5% BSA) | 1.4 centipoise (measured) |
| Hydraulic permeability | ~3 ml/min/100 mm Hg/m² |

Adsorption of mononuclear cells by immunoadsorbent modules

The level of non-specific adsorption of mononuclear cells by immunoadsorbent modules was measured. The cells were collected by apheresis from a patient undergoing stem cell mobilisation. Red cells were removed from the concentrate by centrifuging cells through a Ficol layer. Cells were used within 24 hours of collection and Table 6 gives the experimental details.

TABLE 6

Non-specific adsorption of mononuclear cells collected by apheresis

| Membrane type | Cuprophan F1 |
|---|---|
| Antibody coupling | #9079 oxidised at 20 mM NaIO₄. Final oxidised antibody concentration before coupling = 270 μg/ml |
| Device surface area | 437 cm² |
| Cell loading density | 210,000 cells/cm² |
| Flow protocol | See Table 3 |

The number of cells collected in each fraction was counted using a haemocytometer. Cells were dual stained with antiCD45-FITC and antiCD14-PE (Leukogate, Becton Dickinson) to obtain the relative ratio of lymphocytes and monocytes. A Becton Dickinson Facstar plus was used to analyse cell fractions.

Figure 6:
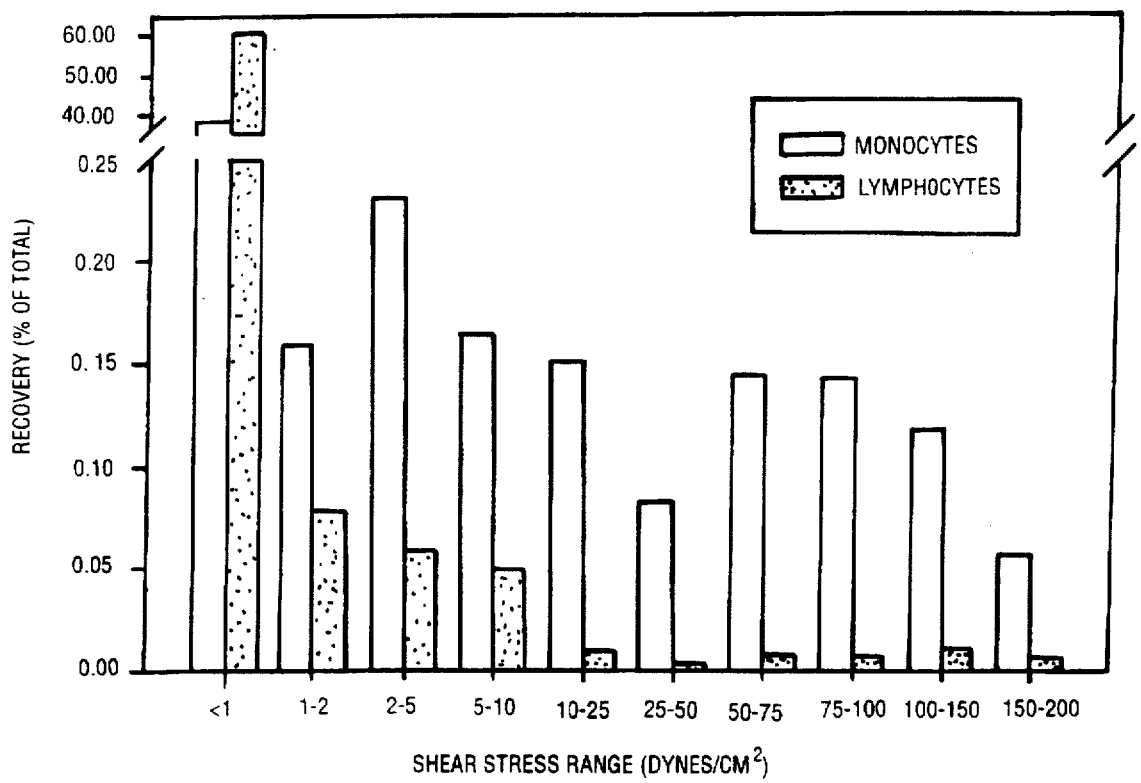
FIG. 6 shows the non-specific absorption of mononuclear cells by an immunoadsorbent module.

FIG. 6 shows the recovery of mononuclear cells as a function of wall shear stress. Cells were incubated with the membrane for 8 minutes before shear fractionation. Recovery was calculated by dividing the number of cells recovered in a faction by the total number of cells eluted in all fractions (i.e. 0–200 dynes/cm²) and expressed as a percentage. About 98% of the total injected population were recovered at 1 dyne/cm² (10 ml). The relative ratio of lymphocytes to monocytes was about 4:6. In subsequent fractions this ratio was inverted, suggesting that monocytes have relative greater affinity for the membrane.

Non-specific adsorption in factions recovered above 10 dynes/cm² was about 0.1–0.15% for monocytes and less than 0.01% for lymphocytes (1 in 10,000). The purity of CD34⁺ cell fractions will depend on the background of non-specific adsorption. Since most of the cells eluting above 10 dynes/cm² will be CD14⁺, purity may be improved by depletion of this subset.

Separation of cell lines

Figure 7:
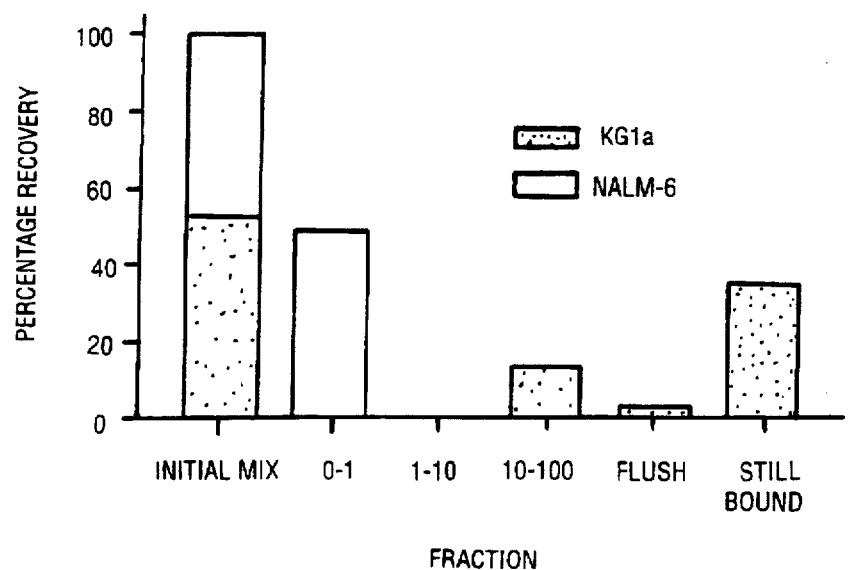
FIG. 7 shows the separation of KG1a (CD34$^+$) from NALM-6 (CD4$^-$) cells using experimental details set out in Table 7.

Initial experiments examined the separation of CD34⁺ cell lines. A CD34⁺ cell-line (KG1a) was separated from NALM-6 (CD34⁻). NALM-6 cells were stained with fluorescein isothiocyanate before mixing with equal numbers of KG1a cells. FIG. 7 shows the numbers of KG1a and NALM-6 cells which were recovered by shear fractionation. Table 7 shows the experimental details for this separation run.

TABLE 7

Separation of KG1a from NALM-6

| Membrane type | Cuprophan F1 |
|---|---|
| Antibody coupling | #9079 oxidised at 20 mM NaIO$_4$. Final oxidised antibody concentration before coupling = 240 µg/ml |
| Device surface area | 219 cm$^2$ |
| Cell loading density | 27,000 cells/cm$^2$. KG1a:NALM-6 = 1.09:1 |
| Flow protocol | 8 minutes membrane contact before shear elution |

Almost all of the NALM-6 cells and only about 2% of KG1a cells were recovered with a shear stress of 1 dyne/cm$^2$. There were relatively few cells recovered in the shear stress range 1–10 dyne/cm$^2$. KG1a cells could be recovered above 10 dynes/cm$^2$. The purity of these fractions was greater than 99.5%. Not all of the KG1a cells were recovered even with vigorous flushing of the module. The fraction of KG1a still bound was estimated by subtraction of the number of KG1a cells recovered from the estimated number of KG1a cells injected.

Number of CD34$^-$ cells injected =

$$\left( \frac{CD34^+}{CD34^-} \right)_{initial\ mix} \times CD34^-_{total\ recovered}$$

The number of injected CD34$^+$ cells may be estimated using the ratio of CD34$^+$/CD34$^-$ from the initial mix.

This experiment demonstrates that the developed immunoadsorbent has high specific affinity for KG1a cells.

To simulate bone marrow, KG1a was added to human buffy coat (~1:100). Table 8 shows the experimental details for this separation. The amount of immobilised antibody (#9079) was similar to that shown in the prior experiment (Table 7), whilst the cell loading density was an order of magnitude greater (290,000 cells/cm$^2$).

TABLE 8

Separation of KG1a from NALM-6

| Membrane type | Cuprophan F1 |
|---|---|
| Antibody coupling | #9079 oxidised at 10 mM NaIO$_4$ (room temperature). Final oxidised antibody concentration before coupling = 270 µg/ml |
| Device surface area | 437 cm$^2$ |
| Cell loading density | 290,000 cells/cm$^2$. 0.64% KG1a positive |
| Flow protocol | 8 minutes membrane contact before shear elution |

Figure 8:
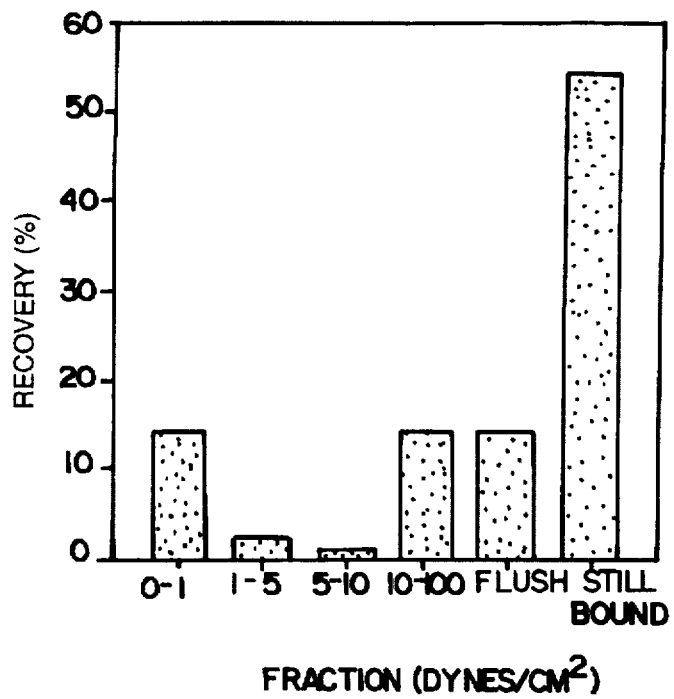
FIG. 8 shows the results of separation and recovery of KG1a cells from buffy coat.
Figure 9:
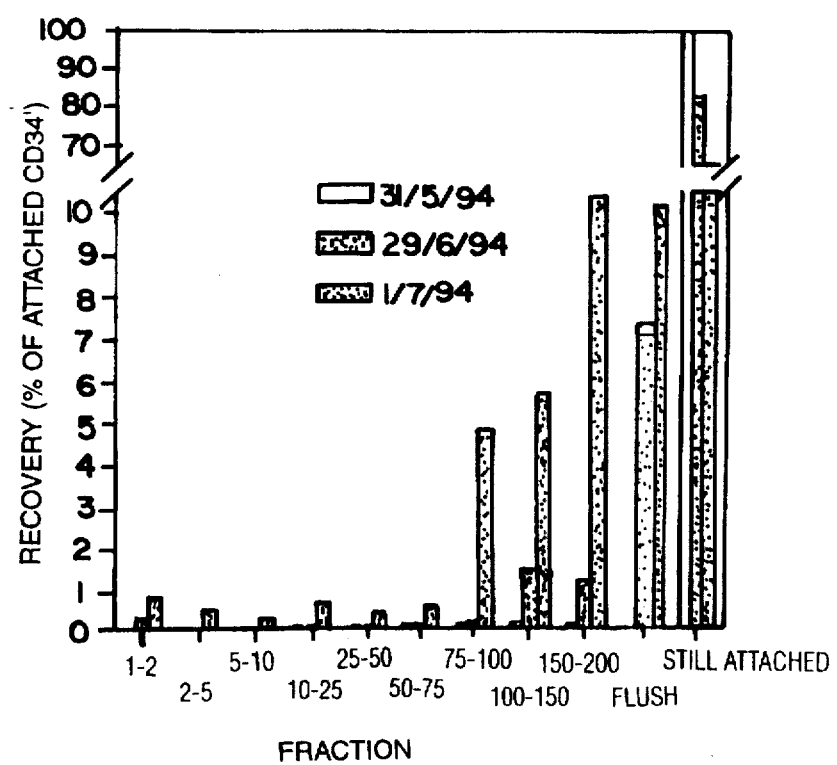
FIG. 9 shows the results of recovery of attached CD34$^+$ cells using fluid shear stress.
Figure 10A:
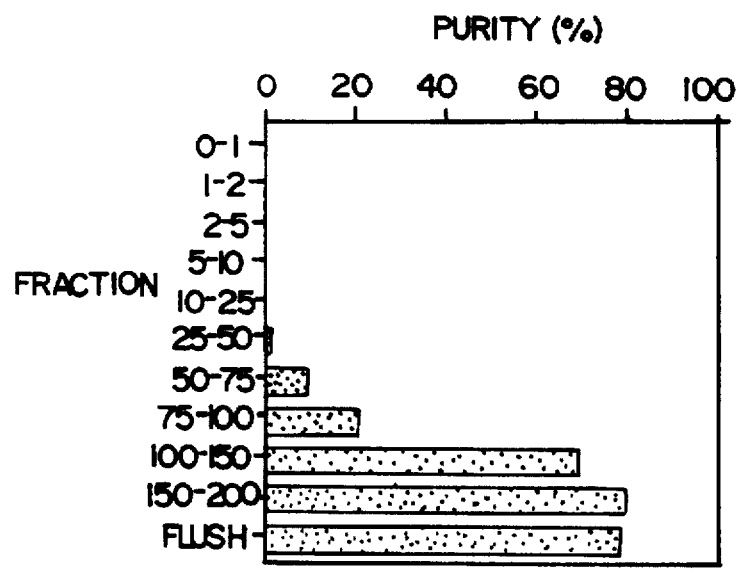
FIGS. 10(a) and 10(b) show the purity and enrichment factor, respectively of cells in experiment No 3 according to the details set out in Table 9.
Figure 10B:
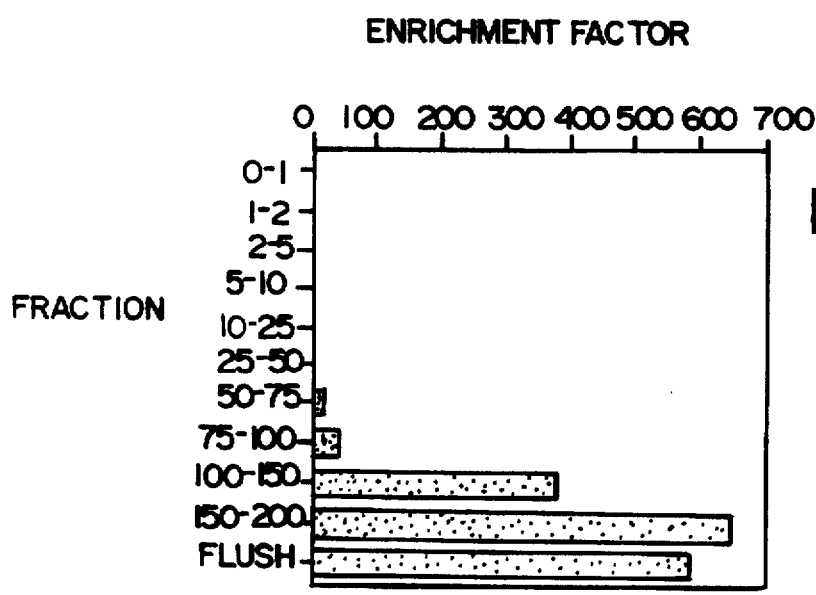

FIG. 8 shows the recover of KG1a cells. Once again there was strong binding of KG1a cells. The attachment probability of KG1a was reduced from 0.98 to 0.85. At higher cell loading densities, the blocking of binding by CD34$^-$ cells is more likely.

Separation of mobilised stem cells (CD34$^+$)

Mononuclear concentrates have been obtained from patients undergoing peripheral stem cell mobilisation using colony stimulating factors at the Royal Adelaide Hospital. Cells are separated within 24 hours of collection. About 200 million mononuclear cells were donated from each harvest (~2×10$^{10}$ cells).

Table 9 shows the experimental details for the first three separation runs. In successive experiments the 25 immunoadsorbent affinity was reduced by lowering the antibody coupling concentration and affinity. #9079 (HPCA-2) has a dissociation constant which is about 10-fold lower than #9069 (9 C5).

TABLE 9

Separation of stem cells from mononuclear cell concentrates

| Experiment | 1 | 2 | 3 |
|---|---|---|---|
| Mobilisation method | SCF + G-CSF Male:myeloma | G-CSF Female:Breast Ca | G-CSF Female:Breast Ca |
| Antibody coupling concentration | #9079 @ 270 µg/ml | #9069 @ 135 µg/ml | #9069 @ 60 µg/ml |
| Cell loading density | 210,000 cells/cm$^2$ | 390,000 cells/cm | 950,000 cells/cm$^2$ |
| Flow protocol | Table 4 | Table 4 | Table 4 |
| Incidence of CD34$^{32}$ cells | 0.2% | 0.56% | 0.61% |
| Attachment probability of CD34$^+$cells | 0.8 | 0.58 | 0.39 |
| % of attached CD34$^+$ cells recovered | 0.9% | 17.5% | 34.2% |

The probability of attachment of CD34$^+$ cells is defined as the proportion of CD34$^+$ cells which remain bound after exposure to a shear stress of 1 dyne/cm$^2$. This is calculated from the incidence of CD34$^+$ cells found in the depleted fraction (0–1 dyne/cm$^2$) and before separation.

$$\text{Attached probability} = \frac{\%\ CD34^+_{initial} - \%\ CD34^+_{depleted}}{\%\ CD34^+_{initial}}$$

In fractions where there was significant recovery of CD34$^+$ cells, there was a purity of 70–80% with high enrichment factors (400–600 fold). CD34$^+$ cells were stained with antiCD34-PE (HPCA-2, Becton Dickinson).

Figure 11:
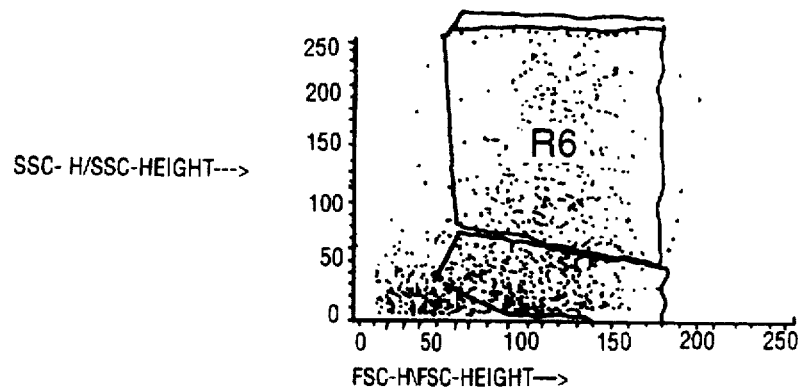
FIG. 11 shows flow cytometric analysis of mononuclear cells before separation carried out in experiment 3.
Figure 11:
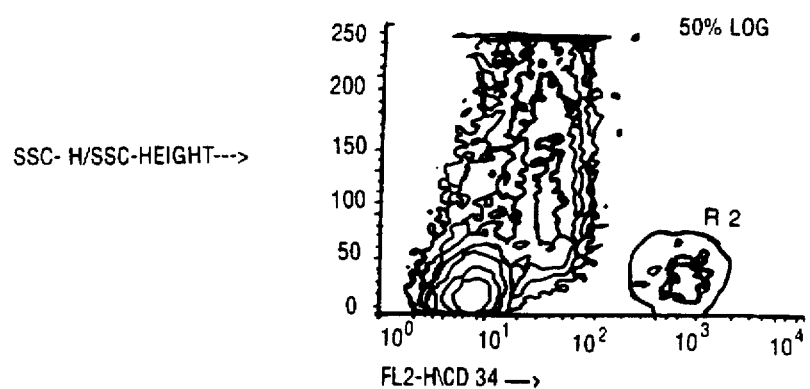
Figure 11:
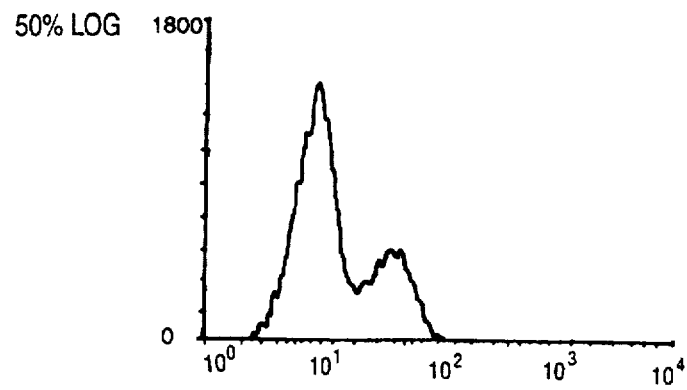

FIG. 11 shows the flow cytometric analysis of the initial cell population from the experiment number 3. The stem cell population is clearly resolved by plotting CD34 fluorescence versus side scatter (see region 2). Regions 7 and 6 were determined using Leukogate (Becton Dickinson), and correspond to the side and forward light scatter properties of lymphocytes (CD45$^+$, CD14$^-$) and monocytes (CD45$^{30}$, CD14$^+$). The percentage of CD34$^+$ cells is expressed as a percentage of the total number of mononuclear cells (R6+R7). The incidence of stem cells was 0.61%.

Figure 12:
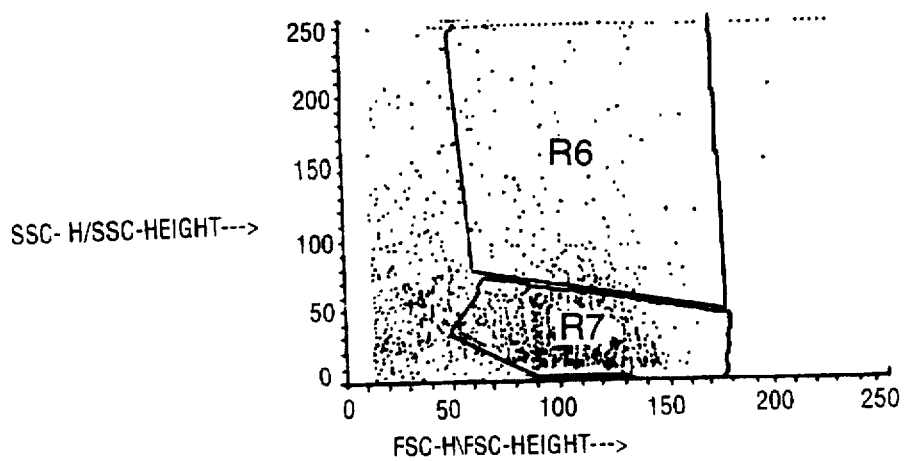
FIG. 12 shows the flow cytometric analsyis of a highly enriched cell fraction from experiment 3 where fraction collection was between 150–200 dines/cm$^2$.
Figure 12:
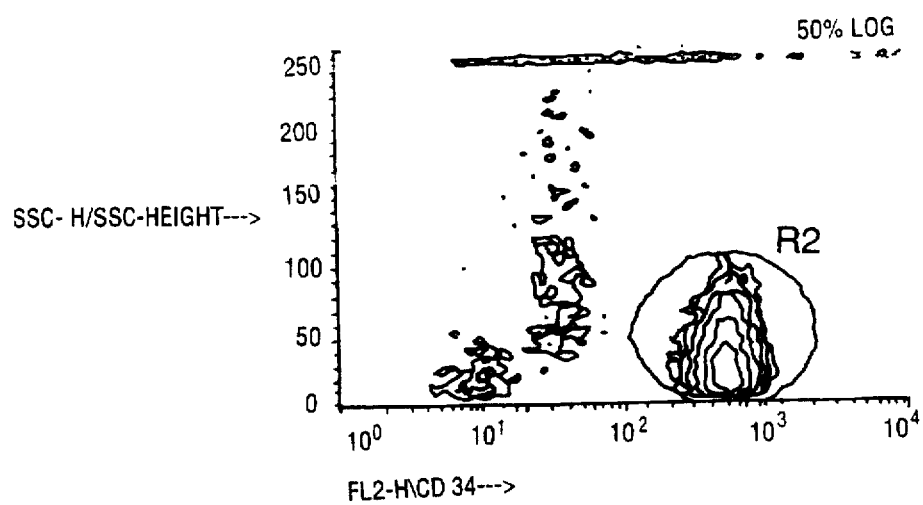
Figure 12:
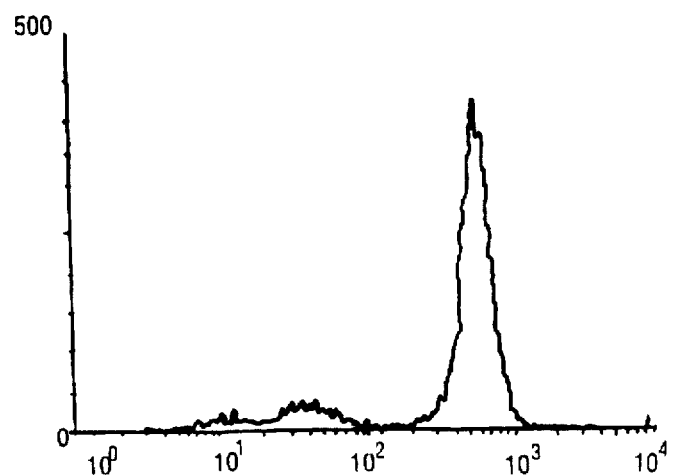

FIG. 12 shows the flow cytometric analysis of a highly enriched fraction from the same experiment. The fraction analysed was collected between 150–200 dynes/cm The incidence of CD34$^+$ cells was 80%. The enrichment factor for this fraction was calculated as follows:

$$\text{Enrichment factor} = \left( \frac{80\%}{20\%} \right)_{recovered\ fraction} \div \left( \frac{0.61\%}{99.39\%} \right)_{initial} = 652$$

Cuprophan is a suitable substrate for affinity cell separation. It has a low level of non-specific cell adsorption, and has a chemistry which is suitable for covalent immobilization of antibody. The developed immunoadsorbents had selective affinity for CD34$^+$ cells (both KG1a and haemopoietic stem cells). Highly enriched CD34$^+$ cell populations may be recovered using shear fractionation.

Attachment probability was lower at high cell loading densities (10$^6$ cells/cm$^2$). Interaction of CD34$^+$ cells with the immunoadsorbent membrane may be blocked by CD34$^-$ cells. Attachment probability at high cell loading densities may be increased by increasing membrane contact times and by slowly rotating the device along its central axis. The rate of antibody-antigen bond formation may also influence cell

SEPARATION OF STEM CELLS (CD34⁺) FROM MOBILIZED BLOOD USING SHEAR FRACTIONATION AND PRE-TREATMENT WITH CHYMOPAPAIN

Cells bound to the semi-permeable substrate of the present invention may be pre-treated with a cell-releasing agent prior to removal by shear stress. The proteolytic enzyme chymopapain has been used to assist the removal of CD34⁺ cells bound to a hollow fibre apparatus of the present invention.

Cell Source

A mononuclear cell concentrate was collected from a patient undergoing peripheral stem cell mobilisation with cyclophosphamide and G-CSF. The initial population had an incidence of 2.74% CD34⁺ cells.

Module chemistry

A Cuprophan hollow-fibre module (binding area ~500 $cm^2$) was derivatised with antiCD34 monoclonal antibody (clone 9e5) using the hydrazide method as described previously with the following change in protocl. Cuprophan was derivatised with 25% ethylene glycol diglycidyl ether for 2 hours at room temperature.

Cell loading

A total of $1.7 \times 10^8$ cells in 4 mls of phosphate buffered saline with 0.5% human Ig and 0.5% bovine serum albumin added was injected into the vertically aligned module using blind-ended filtration. Residual cells in the inlet tubing were flushed with a further 0.5 ml of buffer (blind-ended filtration). The entire loading process took less than 8 minutes. Cells were loaded at approximately 340,000 cells/$cm^2$.

Cell deposition

For cell deposition within the fibre lumen, the module was rotated into the horizontal position. After 4 minutes of settling time, the module was rotated around its long axis over a 12 minute period (2 full revolutions).

Cell recovery

For cell recovery the module was returned to the vertical position. The CD34 depleted cell population was recovered in successive 10 ml fractions by incrementing shear stress up to 100 dynes/cm (Fraction numbers 1–5).

Following this, attached cells were incubated with the proteolytic enzyme Chymopapain (DISCASE™) at 400 pKat/ml. The incubation period lasted 20 minutes. During this time released cells were collected at low shear stress (0.2 dynes/$cm^2$, Fraction 6). Shear fractionation was then used to further purify treated cells. 10 ml fractions were collected at shear stresses of 10, 50 and 100 dynes/cm2.

TABLE 10

Separation of CD34⁺ cells from mobilised blood

| Tube ID | Elution conditions | Total number of cells | DC34⁺ incidence (%) | Number of CD34⁺ cells |
|---|---|---|---|---|
| Before separation | N.A | $1.67 \times 10^8$ | 2.74 | 4,550,000 |
| Fraction 1 | <5 dynes/$cm^2$ | $1.66 \times 10^8$ | 0.77 | 1,280,000 |
| Fraction 2 | 5 dynes/$cm^2$ | 1,380,000 | 1.29 | 17,800 |
| Fraction 3 | 10 dynes/$cm^2$ | 540,000 | 3.58 | 19,300 |
| Fraction 4 | 50 dynes/$cm^2$ | 1,720,000 | 6.89 | 119,000 |
| Fraction 5 | 100 dynes/$cm^2$ | 807,000 | 24.2 | 195,000 |
| Fraction 6 | chymopapain + 0.2 dynes/$cm^2$ | 687,000 | 93.1 | 640,000 |
| Fraction 7 | 10 dynes/$cm^2$ | 2,060,000 | 86.1 | 1,770,000 |
| Fraction 8 | 50 dynes/$cm^2$ | 2,360,000 | 1.91 | 45,100 |
| Fraction 9 | 100 dynes/$cm^2$ | 1,040,000 | 1.19 | 12,400 |
| Fraction 10 | 100 dynes/$cm^2$ | 567,000 | 0.54 | 3,060 |
| Fraction 11 | ~1000 dynes/$cm^2$ (3% dextran T2000) | 660,000 | 0.31 | 2,050 |

Table 10 shows the absolute cell numbers collected in fractions 1–11. Most of the cells were recovered in fraction 1. This fraction was depleted of CD34⁺ cells (CD34⁺= 0.77%). The incidence of CD34⁺ cells increased as the shear stress was increased (fractions 2–5). Most of the CD34⁺ cells were recovered in fractions 6 and 7. The purity of these fractions was at least 90%. Fractions 8–11 have very few CD34⁺ cells.

Figure 13:
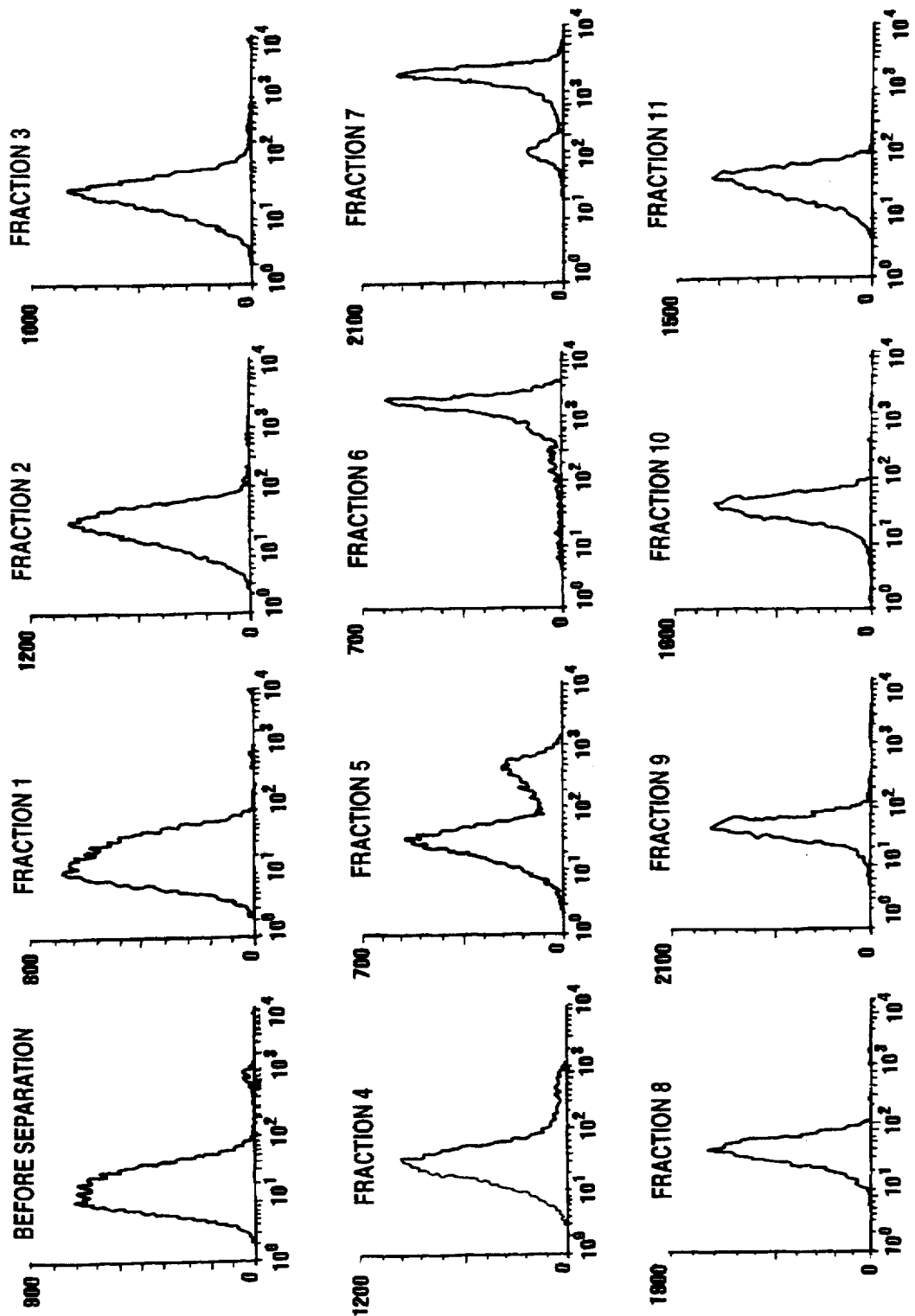
FIG. 13 shows the flow cytometric analysis of CD34 antigen expression in collected fractions.

Attachment probability of CD34⁺ cells was 72%. When fractions 6 and 7 are pooled the separation yield is 53% (CD34⁺ cells recovered/CD34⁺ cells input). CD34 antigen expression FIG. 13 shows the level of CD34 antigen expression in each fraction as determined by flow cytometry (BG12-PE). A uniform gated region was used for determination of the incidence of CD34⁺ cells (see Table 10). CD34⁺ cells collected in fractions 4 and 5 had low levels of antigen expression (channels 100–1000). Chymopapain released cells had higher antigen expression (channels 150–1600). In fraction 7 there were two distinct populations of CD34⁺ cells (channels 50–120 and 120–1600). The lightly staining population appears to be distinct from the typical fluorescence range for CD34⁺ cells (channels 10–100). Therefore the purity of fractions 6 and 7 may have been underestimated by the uniform CD34 gating region adopted (low side scatter and PE fluorescence>channel 105).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

We claim:

1. A method for removing a desired cell type from a sample containing cells including the desired cell type, the method comprising the steps of:

(a) loading the sample into a device including a semi-permeable substrate provided with a ligand reactive with the desired cell type, (b) incubating to allow deposition and binding of the desired cell type to the ligand, (c) treating the semi-permeable substrate in a manner such that the cells not bound to the ligand are removed, and optionally, (d) treating the semi-permeable substrate in a manner such that the cells bound to the ligand are removed.

2. The method as claimed in claim 1 wherein the semi-permeable substrate is selected from the group consisting of cellulose and polyamide.

3. A method as claimed in claim 2 wherein the semi-permeable membrane is cellulose.

4. A method as claimed in claim 1 wherein the semi-permeable substrate is in the form of a hollow fibre.

5. A method as claimed in claim 4 wherein the substrate has a permeability which restricts fluid loss across the substrate to less than 5%.

6. A method as claimed in claim 1 wherein the ligand is selected from the group consisting of an antibody, lectin, growth factor and receptor.

7. A method as claimed in claim 6 wherein the ligand is an antibody.

8. A method as claimed in claim 7 wherein the antibody is a monoclonal antibody.

9. A method as claimed in claim 1 wherein the treatment in steps (c) and (d) comprises shear stress.

10. A method as claimed in claim 9 wherein the cells not bound to the semi-permeable ligand are removed by low shear stress and the cells bound to the semi-permeable ligand are removed by higher shear stress.

11. A method as claimed in claim 9 wherein prior to step (d) the cells bound to the semi-permeable ligand are pre-treated with a cell-releasing agent.

12. A method as claimed in claim 11 wherein the cell-releasing agent is an enzyme.

13. A method as claimed in claim 12 wherein the enzyme is chymopapain.

14. A method as claimed in claim 9 wherein the shear stress is generated by the flow of liquid past the semi-permeable substrate.

15. A method as claimed in claim 9 wherein the shear stress is generated by increasing the viscosity of fluid passing across the semi-permeable substrate.

16. A method as claimed in claim 1 wherein after step (c) the bound cells are maintained under conditions in which the cells divide and multiply.

17. An apparatus for removing a desired cell type from a sample including the desired cell type comprising a semi-permeable substrate in the form of an array of hollow fibres provided internally with a ligand reactive to the desired cell type.

18. An apparatus as claimed in claim 17 wherein the semi-permeable substrate is selected from the group consisting of cellulose and polyamide.

19. An apparatus as claimed in claim 18 wherein the semi-permeable substrate is cellulose.

20. An apparatus as claimed in claim 17 wherein the substrate has a permeability which restricts the fluid loss across the substrate to less that 5%.

21. An apparatus as claimed in any one of claim 17 wherein the ligand is selected from the group consisting of an antibody, lectin, growth factor and receptor.

22. An apparatus as claimed in claim 21 wherein the ligand is an antibody.

23. An apparatus as claimed in claim 22 wherein the antibody is a monoclonal antibody.

24. An apparatus as claimed in claim 17 wherein the hollow fibres are held within a cylindrical module having ports allowing buffer to be circulated around the outside of the fibres and inlet and outlet ports allowing flow of buffer through the fibres.

25. An apparatus as claimed in claim 24 wherein the module is so arranged allowing the flow of buffer along the inside of the fibre being controlled independently from the flux across the fibre.

26. An apparatus as claimed in claim 25 wherein the flow of buffer along the inside of the fiber is provided by a pump means.

\* \* \* \* \*